United States Patent [19]

Dempsey et al.

[11] 4,227,984
[45] * Oct. 14, 1980

[54] POTENTIOSTATED, THREE-ELECTRODE, SOLID POLYMER ELECTROLYTE (SPE) GAS SENSOR HAVING HIGHLY INVARIANT BACKGROUND CURRENT CHARACTERISTICS WITH TEMPERATURE DURING ZERO-AIR OPERATION

[75] Inventors: Russell M. Dempsey, Hamilton; Anthony B. LaConti, Lynnfield; Mary E. Nolan, Topsfield, all of Mass.

[73] Assignee: General Electric Company, Wilmington, Mass.

[ * ] Notice: The portion of the term of this patent subsequent to Oct. 16, 1996, has been disclaimed.

[21] Appl. No.: 16,364

[22] Filed: Mar. 1, 1979

Related U.S. Application Data

[63] Continuation-in-part of Ser. No. 773,012, Feb. 28, 1977, abandoned.

[51] Int. Cl.$^3$ .............................................. G01N 27/46
[52] U.S. Cl. ................................. 204/195 S; 204/1 T; 204/195 R
[58] Field of Search ........... 204/1 T, 1 K, 1 S, 195 R, 204/195 S

[56] References Cited

U.S. PATENT DOCUMENTS 3,776,832  12/1973  Oswin et al. ..................... 204/1 K Primary Examiner—T. Tung
Attorney, Agent, or Firm—I. David Blumenfeld

[57] ABSTRACT

A compact electrochemical gas sensing cell is described for detecting gases such as carbon monoxide, $NO_2$, alcohol vapors, etc. The cell is characterized by temperature stability during zero-air operation so that background current with no gas flow is eliminated or minimized. This cell utilizes a hydrated, solid polymer electrolyte having reference, sensing and counter electrodes mounted on the surface thereof with one side of the membrane being flooded with distilled water to provide self-humidification of the cell by water vapor transport across the membrane. A potentiostatic circuit is utilized to control the potential on the sensing circuit and also to maintain a fixed potential difference between the reference and the sensing electrodes. In addition, the chemical, electrochemical, and thermal characteristics of the sensing and reference electrodes are matched so that the sensor is highly temperature invariant during zero-air operation. The sensing and reference electrodes are so positioned that the resistance of the current path between these electrodes is greater than 60 ohms. Furthermore, the sensing to reference electrode resistance is high compared to the sensing and counter electrode resistance with the ratio being greater than 50 to 1. This essentially places the sensing electrodes outside of the current flux lines between the sensing and counter electrodes. By thus eliminating or substantially reducing any current flow between the sensing and reference electrodes, the changes in background current with temperature during "Zero-Air" operations is sufficiently low (1–3$\mu$ amps) to eliminate the need for temperature compensation during "Zero-Air" operations.

9 Claims, 3 Drawing Figures

POTENTIOSTATED, THREE-ELECTRODE, SOLID POLYMER ELECTROLYTE (SPE) GAS SENSOR HAVING HIGHLY INVARIANT BACKGROUND CURRENT CHARACTERISTICS WITH TEMPERATURE DURING ZERO-AIR OPERATION

The instant invention relates to an electrochemical gas or vapor sensor and, more particularly, to an electrochemical sensor of the SPE type which is very stable with temperature at zero-air operation.

In a contemporaneously filed application, Ser. No. 773,136, (52-EE-0-248) in the name of A. B. LaConti, et al. entitled
Self-Humidifying, Potentiostated, Three-Electrode, Solid Polymer Electrolyte (SPE) Gas Sensor
filed 2-28-77 and assigned to the General Electric Company, the assignee of the present invention, a gas sensing device is described which utilizes a solid polymer electrolyte, is self-humidifying in nature, and is operated in the potentiostatis mode to produce time invariant, high output when sensing gases, such as carbon monoxide, $NO_2$, alcohol, etc. The gas sensing device described in the aforesaid LaConti application for U.S. Letters patent may be further improved to control the thermal characteristics of the cell so that background current is eliminated or reduced to a minimum over a wide range of temperatures in the absence of the gas to be detected, a condition referred to as "zero-air" operation. This may be realized in a cell construction in which the reference and sensing electrodes are preferably positioned on the same side of the membrane and by positioning the reference electrode as close as possible to the sensing electrode while yet maintaining it remote from the flux lines between sensing and counter electrodes. In addition, the electrochemical and chemical characteristics of the electrodes during zero-air operation are matched as closely as possible.

It is therefore, a principal objective of the instant invention to provide a three-electrode, potentiostated electrochemical gas sensor which has excellent temperature characteristics for background current in the absence of detectable gases.

Another objective of this invention is to provide a three-electrode potentiostated electrochemical gas sensor of the solid polymer electrode type with minimal background current over a wide temperature range in the absence of detectable gases.

Still another objective of this invention is to provide an electrochemical gas sensor of the solid polymer electrolyte type with excellent temperature current characteristics under zero-air operation.

A further objective of this invention is to provide an electrochemical gas sensor which does not require temperature compensation for background current during zero-air operation.

Still other objectives and advantages of the invention will become apparent as the description thereof proceeds.

The various objectives and advantages of the invention are realized in an electrochemical gas sensor of the solid polymer electrolyte type in which the sensing and reference electrodes are mounted in close proximity preferably on one side of a membrane. These electrodes and a counter electrode on the other side of the membrane are interconnected by a potentiostatic circuit which maintains the potential at the sensing electrode at the desired level for optinum oxidation or reduction of the gaseous constituent to be sensed and maintains a fixed potential difference between it and the reference electrode. The electrodes are made similar in chemical and electrochemical structure and are secured to the membrane in an identical fashion. The reference and sensing electrodes though mounted in close proximity on the membrane are situated so that the reference electrode is not in the current flux field due to the current driven from the counter to the sensing electrode by the potentiostatic circuit thereby eliminating conditions which give rise to large background current variations with temperature during zero-air operations. This is achieved by maintaining the resistance between the sensing and the reference electrodes in excess of 60 ohms, and the ratio between this resistance and the resistance between the sensing and counter electrodes high, in excess of 50:1.

The novel features which are believed to be characteristic of this invention are set forth in the appended claims. The invention itself, however, both as to organization and mode of operation, together with further objectives and advantages thereof, may be best understood by reference to the following description taken in connection with the accompanying drawings in which:

Figure 1:
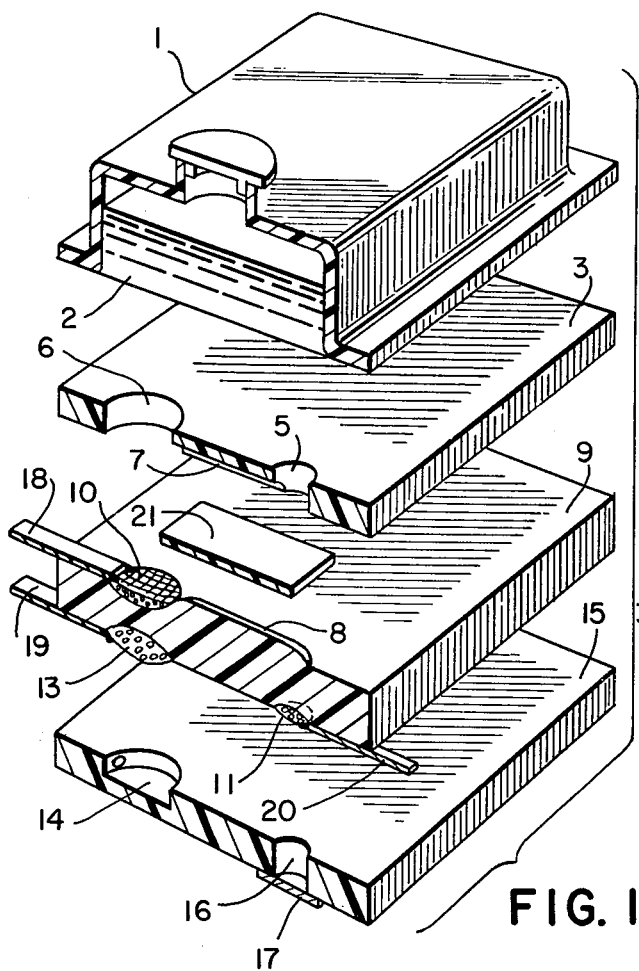
FIG. 1 is an exploded view of a gas sensor cell according to the instant invention.

Operation of the thermally stable, electrically biased, potentiostated, three electrode, electrochemical gas sensor is based on the oxidation or reduction of the constituent to be detected at the catalytic sensing electrode. The sensing electrode is maintained at a potential to produce rapid oxidation or reduction of the gaseous constituent to be detected as, for example, in the case of carbon monoxide oxidation or carbon monoxide to carbon dioxide. The sensing electrode is also biased to maintain the potential at or above the rest potential of an electrode for oxygen or air so that oxidation or a reduction of air has minimal effect on the output of the cell. This may be achieved by utilizing the reference electrode at the rest potential for oxygen and maintaining the sensing electrode at a higher potential than the reference electrode by a fixed amount. The sensing electrode potential must, however, be maintained below that potential at one at which water is dissociated to produce hydrogen and oxygen. For example, in the case of carbon monoxide, the electrode potential for the $CO_2/CO$ redox couple is $-0.12$ volts with reference to platinum/hydrogen reference electrode. By maintaining the potential of the sensing electrode in the range of 1.0 to 1.3 volts, there is rapid and almost immediate oxidation of the carbon monoxide reaching the sensing electrode in accordance with the following reactions at the sensing and counter electrodes.

Sensing Electrode
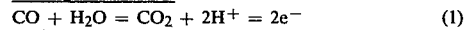
$$CO + H_2O = CO_2 + 2H^+ = 2e^- \qquad (1)$$

Counter Electrode
$$2H^+ + 2e^- = H_2 \qquad (2)$$

or $$2H^+ + \tfrac{1}{2}O_2 + 2e = H_2O \qquad (3)$$

It may be seen from the above reactions that as carbon monoxide is oxidized to carbon dioxide, electrons are released which flow in the external circuit and hydrogen ions are transported through the electrolyte (along with some water molecules) to the counter electrode and are reduced there to form molecular hydrogen or water. The current flowing in the external circuit as a result of this rapid oxidation of carbon monoxide is thus directly proportional to the carbon monoxide concentration.

In the case of CO sensing and with the particular catalyst used here, and presently to be described, by limiting the sensing electrode to potential to 1.3 volts, the potential at the sensing electrode is not sufficiently anodic to oxidize water and introduce errors due to current produced by the oxidation of the $O_2,H^+/H_2O$ couple. That is, the theoretical oxygen/water redox couple is 1.23 volts. However, due to the high overvoltage at the electrode the oxidation of water takes place at some voltage greater than 1.23 volts. For the platinum-5% iridium catalyst used in the instant sensor, there is minimal oxidation of water at 1.3 volts, thereby ensuring that current flow in the sensing cell is due exclusively to the oxidation of the incoming gaseous constituent, such as carbon monoxide. It should also be appreciated that the precise voltage potential at the sensing electrode, reference electrodes, and the range of voltages will differ for differing gaseous constituents to be detected, depending on what the redox for differing gaseous constituents to be detected, depending on what the redox couple for the particular gaseous constituent is to oxidize and reduce that couple, and the range of overvoltages for the particular catalytic electrode.

A potentiostatic circuit is coupled to the reference, sensing and counter electrodes of the cell to maintain the sensing electrode potential at the fixed desired level of 1.1 V versus a platinum/hydrogen reference electrode. There is no interference due to air or oxygen. At the same time, the potential is sufficiently anodic with respect to the carbon monoxide/carbon dioxide couple to produce rapid and immediate oxidation of the carbon monoxide to $CO_2$.

Since the potential level at the sensing electrode plays an important part in determining the magnitude of the output current from the device, it is highly desirable that a good, ionically conductive path is maintained between the sensing and reference electrodes. That is, although ideally no current is supposed to flow between the sensing and reference electrodes with the cell in a potentiostatic mode, there are small currents that do flow between these two electrodes, and may change the potential at the sensing electrode. This could introduce an error because of the change in the oxidation rate at the electrode with changes in the potential. Any change in the differential voltage between the two electrodes also affects the accuracy of the overall indication since background current, particularly at zero-air flow is affected and any increase in background current affects the accuracy of the device. The aforesaid LaConti application described a mechanism for reducing any such IR drop by providing an ionically conductive, hydrated SPE bridge across the membrane between the reference and the sensing electrodes. This ionic bridge maintains a low resistance path between the sensing and reference electrodes. The membrane though hydrated before assembly, may have a tendency to dry somewhat particularly along the surface, thereby increasing the resistance of the membrane and raising the possibility that the electrode potentials may shift due to the IR drop between the sensing and reference electrode. By eliminating this possibility and utilizing an ionically conducting SPE bridge, the output current from the device is substantially enhanced.

Moreover, in addition to enhancement in the output of the device, by maintaining the voltage differential between the two electrodes constant and also positioning and structuring the reference and sensing electrodes in such a manner that the thermal, chemical and electrical characteristics of the two electrodes are as similar as possible, the temperature characteristics of the cell are such that the background current at zero-air operation over a wide temperature range is reduced substantially to a value in the order of 1 or 2 microamperes. For carbon monoxide oxidation the electrodes are similar in chemical composition, preferably platinum black alloys such as a platinum-5% iridium oxide. The electrodes are positioned in the closest proximity possible in order to maintain the same temperature conditions at both of the electrodes, while yet at the same time, positioning the reference electrode away from the current flux lines between the sensing and counter electrode.

FIG. 1 is an exploded perspective view of the gas sensing cell according to the instant invention and shows a reservoir 1 which is filled with distilled water shown generally at 2 which is thus in contact with the upper surface of gasket 3. Gasket 3 contains a pair of hydrated ports 5 and 6 connected on the underside by means of a water channel 7. Channel 7 is positioned over an ionically conductive, hydrated SPE bridge 8 formed internally on the upper surface and in a hydrated, SPE cation exchange membrane 9. Hydration port 5 is aligned spatially with one end of SPE bridge 8 and hydration port 6 is spatially aligned with a counter electrode 10 which is bonded to and embedded in the upper surface of membrane 9. Thus, SPE bridge 8 extends between counter electrode 10 and a catalytic reference electrode 11 bonded to and embedded in the lower surface of membrane 9. Hydration port 6 is somewhat larger in area than counter electrode 10 so that the surface of the counter electrode and the membrane area around the electrode is flooded. Consequently, water in the vapor phase diffuses rapidly through the membrane to the other side in the area of a sensing electrode 13 which is bonded to and embedded in the lower surface of membrane 9 and is spatially in alignment with counter electrode 10. A gas stream containing the constituents to be detected is brought into contact with sensing electrode 13 through a circular sensing port or chamber 14 in the upper surface of a bottom plate 15, with the sensing chamber communicating through suitable channels, not shown, with flow ports not shown, which extend through bottom plate 15. Reference electrode 11 is in direct communication with an opening 16 which is covered with a silicone barrier film 17 so as to permit passage of oxygen or air to the reference electrode while blocking the gaseous constituent, such as CO. Each of the electrodes, reference, counter, and sensing have suitable conductive tabs 18, 19 and 20 attached to the individual electrodes. The tabs are connected to a potentiostatic circuit, presently to be described, to maintain the potential on the sensing constant and to maintain a fixed differential voltage between the reference and sensing electrode to permit invariant and accurate operation with time and with changes in temperature. A tape 21 which has adhesive on both sides is positioned between gasket 3 and membrane 9. The tape is located between the gasket and membrane at a location away from the electrodes and the conductive, hydrated SPE bridge to fasten gasket 3 and membrane 9 securely together. A similar tape, not shown, also having adhesive on both sides, is positioned between the lower surface of membrane 9 and the top side of bottom plate 15. The tape is located between electrode 11 and 7 to secure the membrane to the bottom plate and to block flow of gas between the reference sne sensing electrodes. Water reservoir chamber 1 is securely fastened to gasket 3 by means of a suitable adhesive or adhesive tape between the flanged portion of the reservoir housing and the edges of gasket 3, thereby securing the housing firmly against the gasket and sealing it against leakage.

Figure 3:
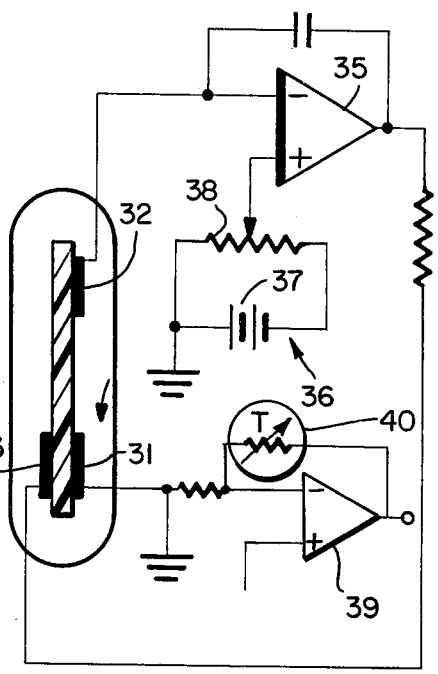
FIG. 3 is a schematic diagram showing the gas sensing cell and a potentiostatic circuit for maintaining reference and sensing electrodes at the desired potentials, as well as a thermistor temperature compensating circuit for compensating the output span signal over the range 1° to 40° C.
Figure 2:
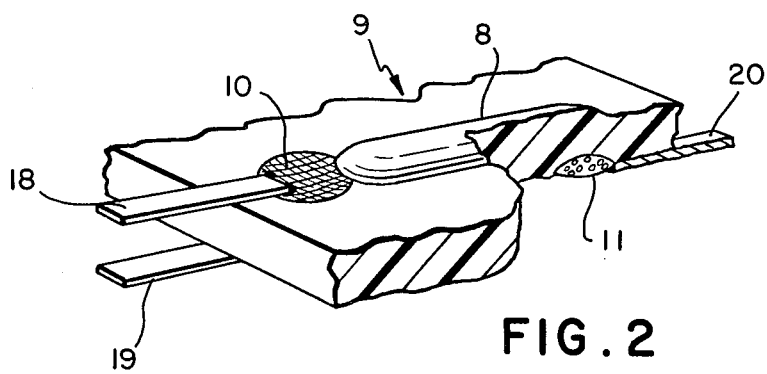
FIG. 2 is a partially broken away view of the solid polymer electrolyte membrane of FIG. 1.

FIG. 3, which is a partially broken away perspective view of membrane 9, shows the counter electrode, the ionically conductive hydrated bridge 8 as well as reference electrode 11 on the lower surface of membrane 9. Thus, it can be seen that counter electrode 10 is bonded to and embedded in the upper surface of the membrane and has a conducting tab extending therefrom beyond the edge of the membrane. The catalytic electrodes, which will be described in detail later, that are used in the CO sensor are each a bonded mass of particles of a platinum-5% iridium alloy and hydrophobic particles such as polytetrafluoroethylene. The bonded mass of catalytic and hydrophobic particles is supported upon and in a metallic, current conducting screen which has the current tab attached to it with the whole assembly in a bonded form being embedded in the surface of the membrane. The membrane includes a swollen, hydrated, ionically conductive SPE bridge 8 which is integral with and extends along and through the membrane along a selected portion of the membrane from counter electrode 10, along the lateral surface of the membrane to a point on the upper surface of the membrane which is spatially aligned with reference electrode 11, which is embedded and bonded along the lower surface of membrane 9. Thus, there is a good ionically conducting path from the sensing electrode 13 (not shown in FIG. 2, which is spatially aligned with counter electrode 10) through the membrane to the counter electrode, along the hydrated, ionically conducting bridge 8 and back through the membrane to reference electrode 11. Thus, there is a low resistance path between the reference and the sensing electrodes, thereby substantially eliminating or minimizing IR drop between the sensing and reference electrodes. By eliminating or markedly minimizing the IR drop through the use of the hydrated bridge, changes in potential at the sensing electrode, as well as changes in the fixed voltage difference to be maintained between the sensing and reference electrodes is eliminated or minimized, thereby minimizing changes which introduce undesirable errors resulting in an instrument which is highly invariant with time, as a high output for even small concentrations of the gas to be detected, and is not subject to background current errors at zero-air operation due to temperature changes.

To summarize, the stable temperature characteristics of the device by means of which background current is reduced to a minimum during zero-air operation over a wide range of temperatures is achieved in a SPE cell by use of a hydrated, ionically conductive bridge in a selected area of the membrane between the sensing and reference electrodes. In addition, the cell is so constructed that the sensing and reference electrodes are preferably on the same side of the membrane, thereby minimizing the distance between the electrodes and any IR drop therebetween.

The reference electrodes is positioned as closely as possible to the sensing electrode so that the ambient temperature for both electrodes is the same.

The reference electrode, though in close proximity to the sensing electrode, must be sufficiently remote from the sensing electrode so that it is not affected by the current flux lines between sensing and counter electrode as the potentiostatic circuit drives current from the counter to the sensing electrode to maintain the electrode potential and voltage differential constant.

For any given membrane thickness and membrane resistance, the reference electrode is positioned relative to the sensing electrode so that the resistance of the path between the sensor and referenced electrode is in excess of 60 ohms and the resistance ratio of sensor to reference and sensor to counter electrodes is in excess of 50. The sensing to reference electrode resistance can vary anywhere between 60 and 180 ohms although a range from 60 to 80 ohms is preferred. The resistance ratio between the electrode pairs may lie between 50–210 although the range between 170–210 is preferred. By maintaining these resistance relationships, it has been found that the temperature characteristics of the cell under "Zero-Air" operation remains essentially invariant for temperature variations of 30°–40° C. That is, with no CO, etc. present the background current varies by no more than 3 micro mperes as the ambient temperature varies by as much as 40° C.

The chemical and electrochemical characteristics of the reference and sensing electrodes should be made as similar as possible by making the catalyst and catalyst structure identical and by attaching the electrodes to the membrane in the same manner.

SPE ION-EXCHANGE MEMBRANE

The solid polymer electrolyte ion-exchange membrane 9, which separates the sensing electrode from the counter electrode, is characterized by ion transport selectivity. Being a cation exchange membrane, it permits passage of positively charged ions, i.e., cations, and rejects and blocks passage of negatively charged ions, i.e. anions. Thus, the hydrogen ions produced at the sensing electrode through oxidation of carbon monoxide are transported through the ion-exchange-membrane (along with some attached water molecules) to the counter electrode where they are reduced by the addition of electrons to produce molecular hydrogen or water. As pointed out in the aforementioned LaConti et al application, of the many classes of ion-exchange resins and membranes, the preferred one is a perfluorocarbon sulfonic acid membrane because of the excellent ion exchange capacity of such a membrane, its high stability, its resistance to acids and strong oxidants and its excellent thermal stability. In addition to these very desirable chemical and physical properties the perfluorocarbon sulfonic acid membranes are essentially invariant with time and thus will not degrade. A preferred form of such cation membrane is one in which the polymer is a hydrated copolymer of polytetrafluoroethylene (PTFE) and polysulfonyl fluoride vinyl ether containing pendant sulfonic (SO₃−H+) acid groups. The sulfonic groups are chemically bound to the perfluorocarbon backbone so that the concentration of the electrolyte remains fixed. After equilibrating the membrane by hydrating it through soaking in 100° C. water for 30 minutes, the structure of the sulfonated perfluorocarbon is as follows:

The ionic conductivity of this particular solid polymer electrolyte, which is sold by the DuPont Company under its trade designation "Nafion" is provided by the mobility of the hydrated hydrogen ions (H+ × H₂O).

Electrodes 10, 11, and 13 in the form of a decal of catalytic material mounted on a current collecting screen are integrally bonded to and embedded in the surface of the polymeric cation exchange membrane. One process for doing so is described in detail in U.S. Pat. No. 3,134,697 entitled "Fuel Cell", issued May 26, 1964 in the name of L. W. Niedrach and assigned to the General Electric Company, the assignee of the instant application. Briefly speaking the electrode structure is forced into the surface of a perfluorocarbon ion-exchange membrane, thereby integrally bonding the gas absorbing hydrophobic particle-catalyst mixture to and embedding it into the surface of the solid polymer electrolyte ion-exchange membrane. Thereafter, the membrane is further processed to form the ionically conductive hydrated SPE bridge located over a selected portion of the membrane. To this end, the membrane is swollen by further hydration through an "in situ" addition of boiling water (preferably 3 additions, 10 minutes apart). That is, boiling water is poured into the hydration ports and allowed to pass through water channel 7 which is coextensive with the area of the membrane which is to be swollen to form the ionically conductive, hydrated SPE bridge. Thus, the area underneath the hydration channel which extends generally between the counter electrode and the spatial projection of the reference electrode is bonded to the lower surface of the membrane underneath the water channel, both along the surface and through the body thereof, to produce a bridge and an ionically conductive path between the reference and sensing electrodes. As pointed out above, the procedure may be repeated one or more times with the preferred number being 3 times 10 minutes apart.

Also, as pointed out in the aforesaid LaConti application, the sensor is self-humidifying in nature because portions of one side of the membrane are flooded with distilled water. This water is transported in the vapor phase across the membrane, the membrane should have the highest possible water content, i.e., the highest possible ion-exchange capacity (IEC). The IEC and hence the water content of the membrane is controlled by making the MeQH+/gram of dry membrane as high as possible. For a sulfonated perfluorocarbon membrane of the type referred to above, excellent water vapor transport will be achieved if the membrane has an Meq/gram of dry membrane in the range 0.83 to 0.95.

CATALYTIC ELECTRODES

The cell electrodes, as referred to briefly above, are gas permeable, noble metal alloy or graphite catalytic electrodes, comprising catalyst particles bonded to particles of a hydrophobic polymer such as polytetrafluoroethylene. The catalytic electrodes for CO oxidation are preferably a bonded mixture of reduced oxides of a platinum-5% iridium alloy and of PTFE hydrophobic particles. Reference is hereby made to U.S. Pat. No. 3,992,271, Ivan F. Danzig, et al, issued Nov. 16, 1976, and assigned to the General Electric Company, the assignee of the present application for a detailed description of the fabrication process for reduced oxides of platinum-iridium. Briefly, the platinum-5% iridium catalyst, which consists of reduced oxides of the platinum-iridium alloy, is prepared by thermally decomposing mixed metal salts of the elements of the alloy. The actual method of preparation, which is a modification of the Adams method of platinum preparation, involves addition of a thermally decomposable iridium halide such as iridium chloride to platinum chloride. In one example, finely divided halide salts of platinum and iridium are mixed in the same weight ratio of platinum and iridium as it is desired in the final alloy. An excess of sodium as NaNO₃ is incorporated and the mixture fused in a silica dish at 500° C. for three hours. The residue is thoroughly washed to remove any nitrates and halides present. The resulting suspension of mixed oxide is reduced a room temperature by using an electrochemical reduction technique. The product is dried thoroughly and then ground and sieved through a mesh screen. The reduced oxides of platinum-5% iridium thus produced are then bonded with hydrophobic polytetrafluoroethylene particles.

The nature and characteristics of an electrode, comprising a mixture of particles of a gas absorbing noble metal bonded with particles of hydrophobic material as well as the process for doing so, are described in detail in U.S. Pat. No. 3,432,355, entitled "Polytetrafluoroethylene Coated and Bonded Cell Structure", issued Mar. 11, 1969 in the name of Leonard W. Niedrach, et al, which patent is assigned to the General Electric Company, the assignee of the present application, and in U.S. Pat. No. 3,297,484, entitled, "Electrode Structure and Fuel Cell Incorporating the Same", issued Jan. 10, 1967, also in the name of L. W. Niedrach and also assigned to the General Electric Company, the assignee of the present application.

The bonded electrode structure which has been prepared in accordance with the procedure described in Niedrach U.S. Pat. No. 3,432,355 is bonded to and embedded into the surface of the membrane by means of the process described in U.S. Pat. No. 3,134,697 above.

FIG. 3 illustrated schematically the manner in which the electrodes of an SPE gas sensor are coupled to a potentiostatic circuit which maintains the potential at the sensing electrode constant at the desired level and maintains the proper potential difference between the sensing and reference electrodes. FIG. 3 also shows temperature compensating circuitry coupled to the output of the cell for processing the output signal to compensate for changes in the output current over the operating or span range as a result of temperature variations. No temperature compensation of the cell for background current during zero-air operation when none of the gaseous constituents are being sensed is required.

Potentiostatic devices are well-known in the art and only a limited description thereof will be provided in connection with FIG. 3 for the sake of completeness. Thus, the SPE sensor is shown generally at 30 and includes a solid polymer electrolyte ion-exchange-membrane having a sensing electrode 31, a reference electrode 32 on one side of the membrane and a counter electrode 33 on the other side. Reference electrode 32 is coupled to the inverting input terminal of operational amplifier 35 and is compared to a reference voltage from a DC supply source 36 which is applied to the non-inverting input of amplifier 35. Source 36 includes a battery or similar power source 37, the positive terminal of which is grounded as is the sensing electrode 31. A potentiometer resistor 37 is connected across battery 36 and has a slider which is connected to the non-inverting terminal. The position of the slider is adjusted to the voltage at which the sensing electrode with respect to the reference electrode is to be maintained. Thus, in the case of the carbon monoxide sensor, reference electrode Pt/Air ($O_2$) 32 is at approximately +1.05 V. With a voltage differential of +50 mv between the sensing and reference electrode, the sensing electrode is maintained at +1.1 volts with respect to a platinum/$H_2$ reference electrode.

The potentiostatic circuit thus shown in FIG. 3 senses the voltage between the reference and sensing electrode and compared it to the preset value at potentiometer/slider. Changes at the sensing electrode due to the oxidation of carbon monoxide or any other gas causes a change in the relative potential between the sensing and reference electrode. This, in turn, causes the sensing electrode to shift with respect to the fixed reference voltage at the potentiometer slider and the output current from operational amplifier 35 drives a current between counter electrode 33 and sensing electrode 31 to return the potential at the sensing electrode to the desired constant level and returns the differential voltage between the electrodes to the desired 50 millivolts. The current required to drive the system to null balance is a measure of the concentration of the gas being sensed.

Rather than measuring the current directly at the output of the cell, it will be desirable in many cases to provide temperature compensation of the cell output current over the normal operating range of the cell, i.e., the operating or "span" current which varies with temperature. Hence, the output current, which is driven through the counter electrode to the sensing electrode, is converted to a voltage proportional to the current flow and applied to the inverting input of an operational amplifier 39 which has a temperature responsive device such as a thermistor 40 connected in a feedback path between its output and the inverting input. A reference voltage from a reference source, not shown, is applied to the non-inverting input terminal of operational amplifier 39. The characteristic of the thermistor is such that its resistance varies with temperature over a given range and the slope of the resistance variations is exactly opposite to the slope of the output or "span" current over the given temperature range. Hence, a negative feedback voltage is provided at the input of the operational amplifier which controls the amplifier gain so as to cancel the error in the output from the cell voltage which is due to changes in temperature. The output of the operational amplifier 39 is a signal which is compensated over the "span" range for variations due to temperature.

As has been pointed out previously, the voltage at the sensing electrode with respect to platinum/hydrogen reference electrode is limited to the range roughly between 1.0 volts and 1.3 volts with the preferred voltage level being 1.1 volts. The upper voltage is limited to a maximum of 1.3 volts to avoid oxidation of water since this water reaction competes with oxidation of carbon monoxide reaction and introduces current flow which produces errors in the instrument output. The voltage should not be allowed to fall below approximately 1.0 volts in order to maintain an oxide coating on the surface of the catalytic sensing electrode to prevent CO poisoning of the electrode and to prevent reduction of oxygen at the electrode or other competing reactions which introduce error currents. That is, at 1.0 volts or above, the platinum-5% iridium reduced oxide alloy has a thin oxide surface of the catalyst is removed and there is a risk of carbon monoxide poisoning. Furthermore, below 1.0 volts there is a possiblity that oxygen may be reduced at the electrode thus introducing a competing reaction which results in current flow that is not representative of carbon monoxide oxidation.

In order to illustrate the manner in which a SPE cell utilizing a conductive bridge which is constructed with the reference and sensing electrodes positioned in close proximity, but outside of the current flux lines between sensing and counter electrodes, results in improved temperature characteristics for the cell, a number of cells were built utilizing liquid electrolytes and were tested to determine what the background current was for such a liquid electrolyte potentiostated cell over a given temperature range. Thereafter, cells were built in accordance with the instant invention and the background current measured over the same temperature range to compare the temperature response characteristics of a cell made in accordance with the invention and one which utilizes a liquid electrolyte.

EXAMPLE 1

First, a cell was constructed which had a sensing electrode mounted on one side of a fiberglass matrix which was saturated with a 25% sulfuric acid solution (25% $H_2SO_4$). A sensing electrode was positioned between the matrix between the sensing electrode and a counter electrode positioned on the opposite side of the matrix. The sensing reference and counter electrodes were all platinum-5% iridium platinum catalytic electrodes. The cell was potentiostated to maintain the sensing electrode at 1.1 V and sensing electrode was exposed to air flowing at 30 cc's per minute. The ambient temperature to which the cell was exposed was varied from 10 to 40° C. The background current varied roughly 1 microamp at 10° C. to approximately 17 microamps in the vicinity of 40° C. Thus, a background current variation of 15 microamps was generated with zero-air flow condition, i.e., in the absence of any gaseous constituent which is to be detected. Thereafter, a cell of similar construction was built but utilizing a 37% phosphoric acid electrolyte ($H_3PO_4$); same kind of electrodes, same air feed, etc., the background current again varied roughly from ½ microamp to 16 microamps over a range from roughly 10° C. to slightly over 45° C.

EXAMPLE 2

Thereafter, cells were constructed in accordance with the instant invention utilizing a sulfonated perfluorocarbon of the type sold by DuPont under its trade designation, Nafion, utilizing Pt-5% iridium catalytic electrodes for sensing, counter and reference electrodes. The reference electrode was located outside of the current flux path between the sensing electrode. Both reference and sensing electrodes were bonded to and embedded in the surface of the membrane by the process described previously, and the membrane on the counter side of the membrane was treated with boiling water to produce an ionically conductive bridge by swelling the membrane with the bridge extending generally from the counter electrode. The cells were tested using a Wenking 61S potentiostat with a 50 mv voltage difference maintained between the reference and sensing electrodes and the sensing electrode at 1.1 volts. The cells were run on ambient air, 18 ppm carbon monoxide and air, and 53 ppm carbon monoxide and air at 3° C., 25° C., and 40° C. A summary of the test results is shown in the following table:

| Feed Concentrate | Output Signal ($\mu a$) | | |
|---|---|---|---|
| ppm CO in Air | T= 3° C. | T= 25° C. | T= 40° C. |
| 0 ppm | 1-2 | 1 | 2.5 |
| 18 ppm | 12 | 19 | 27 |
| 53 ppm | 37 | 53 | 72 |

It will be seen from the data that the effect of temperature on background at zero-air flow conditions is considerably less than for liquid electrolyte cells for which data was presented previously. That is, the background current over at 37° C. temperature range stayed between 1 and 2½ microamps, as opposed to ½ to roughly 17 microamps for liquid electrolyte cells. With a background current which is in the range of 1 to 2 microamps, it is not necessary to provide zero compensation for the cell, i.e., temperature compensation for the cell when operating on zero-air with no constituent of the gas to be detected present.

EXAMPLE 3

A cell with a hydrated swollen, ionically conductive bridge was constructed utilizing Pt-5Ir reference and counter electrodes and a Teflon bonded, graphite, sensing electrode. The applied voltage at the sensing electrode was 0.7 volts. An air feed containing 20.6 ppm of $NO_2$ with feed flow rate of 40 cc/min was supplied. The instrument was tested at various temperatures to determine background current at zero-air operation and with $NO_2$ present. The following results were obtained:

| T (° C.) | Signal ($\mu a$) with Air Flow Only (Zero-Air) | Signal ($\mu a$) with 20.6 ppm $NO_2$ |
|---|---|---|
| 8° C. | 0 | −31 |
| 26° C. | 0 | −39 |
| 37° C. | −1 | −46 |

It is apparent again that excellent background current characteristics are obtained at zero flow conditions with background limited at 0–1 $\mu$ amps over a 30° C. temperature range. The "span" current does show temperature variations which require temperature compensation.

EXAMPLE 4

A plurality of cells were constructed utilizing a 12 mil (0.30 millimeters) thick sulfonated per fluorocarbon of the type sold by DuPont under its trade designation Nafion. The sensing, counter, and reference electrode were each platinum-5% iridium catalytic electrodes bonded directly to the surfaces of the membrane with the sensing and reference electrode being on one side of the membrane. The sensing and counter electrodes were 1.6 cm in diameter and the reference electrode 0.6 cm in diameter. The spacing between the reference and the sensing electrodes was 1 millimeter. The membrane was treated in the manner described in Examples 1-3 by swelling the membrane to produce an ionically conductive bridge extending generally from the counter electrode to a location opposite to and spatially aligned with the reference electrode. The cells were tested using a Wenking 61S potentiostat to maintain a 50 milivolt voltage difference between the reference and sensing electrodes with the sensing electrode being maintained at 1.1 volts and the reference at 1.05 volts. The resistance of the path between the sensing and reference electrodes and between the sensing and counter electrodes was measured with a 1000 AC bridge. The cells were than tested by measuring the background current at "Zero-air" operations i.e. in the absence of selected gas such as carbon monoxide, as the temperature varied from 3° to 40° C. in one instance and up to 33° C. in the other instance. The summary of these tests is shown in the following table in which the resistances and the resistance ratios of the various cells are illustrated and further in which the background current with temperature is illustrated for two of the cells described in the first table:

TABLE I

| Cell | Electrode to Electrode Resistance (in ohms) | | Resistance Ratio |
|---|---|---|---|
| | Sensing to Reference | Sensing to Counter | |
| A | 74 | 0.41 | 181 |
| B | 73 | 0.35 | 209 |
| C | 75 | 0.43 | 174 |
| D | 73 | 0.43 | 170 |
| E | 60 | 0.30 | 180 |
| F | 157 | 3.1 | 51 |

TABLE II

| Cell | CO Concentration | Temperature | Current (in $\mu$ amps) |
|---|---|---|---|
| E | 0 ppm | 26° C. | 1 |
| E | 0 ppm | 40° C. | 2–3 |
| F | 0 ppm | 3–4° C. | 1–2 |
| F | 0 ppm | 25° C. | 2–3 |
| F | 0 ppm | 33° C. | 4–5 |

It is apparent from the data that the effect of temperature on background current at "zero-air" flow condition is minimal over the entire temperature range varying approximately 3 microamps with a temperature swing of 30°–40° C. with a maximum background current of 4–5 microamps at the extreme temperature excursion.

The inter electrode resistances of a gas sensing cell with a liquid electrolyte system, as described in Example 1 were than measured and the resistance ratio between the electrode pairs obtained. It was found that the sensing to reference electrode resistance was 11 ohms and the sensing to counter electrode resistance was 20 ohms so that the resistance ratio was 0.5. As shown in Example I a liquid electrolyte sensor of this sort is subject to wide temperature induced background current fluctuations under "zero-air" conditions; background current fluctuations of 17 microamps with a 30°–40° C. temperature swing.

It is thus clearly apparent that an improved, compact gas sensor has been provided which utilized solid polymer electrolytes having an integral ionically conductive bridge between a reference and sensing electrode which has excellent temperature characteristics in the zero-air mode of operation, i.e., the response when there are no gas molecules to be sensed present at the sensing electrode. This therefore, allows operation of the cell without any temperature compensation means for zero-air operation.

While an embodiment of this invention has been shown and described, it will be understood, of course, that the invention is not limited thereto, since many other arrangements, both in the device and structure and in the process steps, may be employed. It is contemplated by the appended claims to cover any such modifications that fall within the true scope and spirit of this invention.

What is claimed as new and desired to be secured by Letters Patent of the United States is:

1. In a temperature invariant electrochemical, gas-sensing device the combination comprising:
   (a) an ion transporting membrane;
   (b) catalytic sensing and counter electrodes positioned on opposite sides of said membrane;
   (c) a catalytic reference electrode positioned on the same side of the membrane as said sensing electrode;
   (d) an ionically conductive, low-resistance path between said counter electrode and an area which is spatially aligned with the reference electrode but on the opposite side of said membrane, said membrane having been treated on said opposite side to provide said low resistance path;
   (e) potentiostatic circuit means coupling the sensing, reference and counter electrodes for maintaining the potential at the sensing electrodes constant and for maintaining a fixed potential difference between the sensing and reference electrodes to maintain the device insensitive to the carrier gas for the constituent to be sensed;
   (f) means for exposing the sensing electrode to a carrier gas stream containing the gaseous constituent to be sensed;
   (g) means for measuring the current flowing between the counter and sensing electrode to maintain the sensing electrode potential constant, said current being a measure of a concentration of the selected gaseous constituents.
   (h) means to maintain background current substantially constant with varying temperatures including means maintaining the resistance between the reference and sensing electrodes greater than 60 ohms means and maintaining the ratio of sensing to reference and sensing to counter electrode resistances in excess of 50 whereby the background current changes with temperature in the absence of the gaseous constituent to be sensed are minimized.

2. The gas-sensing device according to claim 1 wherein the resistance between the reference and sensing electrodes is between 60 and 160 ohms.

3. The gas-sensing device according to claim 1 wherein the resistance between the reference and sensing electrodes is between 60 and 80 ohms.

4. The gas-sensing device according to claim 1 wherein the resistance ratio of the sensing to reference and sensing to counter electrode resistances is between 50–210.

5. The gas-sensing device according to claim 1 wherein the ratio of sensing to reference and sensing to counter electrode resistances is between 170 and 210.

6. The gas-sensing device according to claim 2 wherein the ratio of sensing to reference and sensing to counter electrode resistances is the range of 50–210.

7. The gas-sensing device according to claim 2 wherein the ratio of sensing to reference and sensing to counter electrode resistances lies in the range of 170–210.

8. The gas-sensing according to claim 3 wherein the ratio of sensing to reference and sensing to counter electrode resistances lies in the range of 50–210.

9. The gas-sensing device according to claim 3 wherein the ratio of sensing to reference and sensing to counter electrode resistances lies in the range of 170–210.

* * * * *